United States Patent
Lu et al.

(10) Patent No.: US 9,931,280 B2
(45) Date of Patent: Apr. 3, 2018

(54) DENTAL COMPOSITE COMPOSITIONS FOR REDUCED SHRINKAGE STRESS

(71) Applicant: DENTSPLY INTERNATIONAL INC., York, PA (US)

(72) Inventors: Hui Lu, Magnolia, DE (US); Xiaoming Jin, Middletown, DE (US); Joachim E. Klee, Radolfzell (DE); Bernard Koltisko, Milton, DE (US)

(73) Assignee: Dentsply Sirona Inc., York, PA (US)

( * ) Notice: Subject to any disclaimer, the term of this patent is extended or adjusted under 35 U.S.C. 154(b) by 22 days.

(21) Appl. No.: 14/505,687

(22) Filed: Oct. 3, 2014

(65) Prior Publication Data
US 2015/0099821 A1    Apr. 9, 2015

Related U.S. Application Data

(60) Provisional application No. 61/886,246, filed on Oct. 3, 2013, provisional application No. 61/886,747, filed on Oct. 4, 2013.

(51) Int. Cl.
| | |
|---|---|
| *A61K 6/08* | (2006.01) |
| *A61K 6/083* | (2006.01) |
| *C07D 295/24* | (2006.01) |
| *A61K 6/00* | (2006.01) |

(52) U.S. Cl.
CPC ............ *A61K 6/083* (2013.01); *A61K 6/0008* (2013.01); *C07D 295/24* (2013.01)

(58) Field of Classification Search
CPC ...... A61L 6/083; A61L 6/0008; A61L 6/0073; C07D 295/214; C08L 33/00; C08L 33/10
See application file for complete search history.

(56) References Cited

U.S. PATENT DOCUMENTS

| | | | |
|---|---|---|---|
| 4,581,429 A | 4/1986 | Solomon et al. | |
| 5,847,025 A | 12/1998 | Moszner et al. | |
| 7,659,324 B2 * | 2/2010 | Moszner | A61K 6/0017 433/228.1 |
| 8,026,295 B2 | 9/2011 | Walz et al. | |
| (Continued) | | | |

FOREIGN PATENT DOCUMENTS

| | | |
|---|---|---|
| WO | 01/60322 A1 | 8/2001 |
| WO | 2010/114760 A1 | 10/2010 |

OTHER PUBLICATIONS

Shaabin, Maram. The effects of inhibitor and initiator concentration on degree of conversion, flexural strength, and polymerization shrinkage stress on resin-matrix composites. [online]. Retrieved online on [Oct. 8, 2017]. Retrieved from internet: <URL:https://scholarworks.iupui.edu/handle/1805/2113>.*

(Continued)

*Primary Examiner* — Sanza Mcclendon
(74) *Attorney, Agent, or Firm* — McNees Wallace & Nurick LLC

(57) ABSTRACT

A dental composite composition is disclosed that includes a polymerizable resin, filler particles, and at least one polymerizable stable radical. A variety of polymerizable stable radicals may be employed, including those that have a 2,2,6,6-tetramethylpiperidinyl-1-oxyl moiety. Compositions as described herein exhibit excellent mechanical strength, hardness, and flexural modulus, while also significantly decreasing shrinkage stress caused by polymerization.

20 Claims, 5 Drawing Sheets

(56) References Cited

U.S. PATENT DOCUMENTS

| | | | | |
|---|---|---|---|---|
| 8,552,087 | B2* | 10/2013 | Zappini | A61K 6/0044 433/225 |
| 2004/0131995 | A1 | 7/2004 | Klee et al. | |
| 2012/0129973 | A1* | 5/2012 | Sun | A61K 6/02 523/115 |

OTHER PUBLICATIONS

Braga, R. R., & Ferracane, J. L. (2002). Contraction stress related to degree of conversion and reaction kinetcis. Journal of Dental Research, 81(2), 114-8. Retrieved from https://search.proquest.com/docview/209466851?accountid=14753 (Year: 2002).*

Schneider, L. F. J., Cavalcante, L. M., & Silikas, N. (2010). Shrinkage Stresses Generated during Resin-Composite Applications: A Review. Journal of Dental Biomechanics, 2010, 131630. http://doi.org/10.4061/2010/131630 (Year: 2010).*

XP002733835, A.A. Dubinski et al., "Determination of the Distance Between the Pargamagnetic Fragments in Biradicals from the Forbidden Transition", Inst. Chem. Phys., vol. 19, No. 5, 1974.

H. Lu, C. N. Bowman, J. W. Stansbury, Dental Materials, 2004, vol. 20, 979-986.

J. W. Stansbury, Dental Materials, 2012, vol. 28, 13-22.

Moad G, Rizzaardo E, Thang SH, Australian Journal of Chemistry 2005, vol. 58, 379-410.

H. Gao, K. Matyjaszewski, Progress in Polymer Science, 2009, vol. 34, 317-350.

J.C. Hernandez-Ortiz et al, Macromolecular Reaction Engineering, 2009, vol. 3, 288-311.

G.V. Korolev et al, Polymer Science, Ser A, 2001, vol. 43, 482-289.

G E. Tuinman et al, Journal of Macromolecular Science, Part A, 2006, vol. 43, 995-1011.

C.S. Pfeifer, N.D. Wilson, Z.R. Shelton, J.W. Stansbury; Polymer 2011, vol. 52, 3295-3303.

H. Lu et al., Journal of Materials Science, Materials in Medicine, 2004, vol. 15, 1097-1103.

K. Leinfelder, S. Suzuki, Journal of American Dental Association, 1999, vol. 130, 1347-1353.

Steeman PAM, Dias AA, Wienke D, Zwartkruis T, Macromolecules, 2004, vol. 37, 7001-7007.

J. W. Stansbury, et al, Dental Materials, 2005, vol. 21, 56-67.

\* cited by examiner

DENTAL COMPOSITE COMPOSITIONS FOR REDUCED SHRINKAGE STRESS

RELATED APPLICATIONS

This application claims the benefit of and priority to U.S. App. No. 61/886,246 filed Oct. 3, 2013, and U.S. App. No. 61/886,747 filed Oct. 4, 2013, both of which are hereby incorporated by reference in their entirety.

BACKGROUND

Dental composites with excellent tooth-like appearance can be formed on command with the advance of photopolymerization technology. Yet compared with that of the traditional amalgam filling materials, the longevity and robustness of current dental composites are still not ideal. Well-preserved interfacial bonding between the composite and tooth is of vital importance to prevent the occurrences of compromised marginal adaptation, microleakage, and recurrent caries. Restricted polymerization shrinkage, as one of the major drawbacks of dental composites, results in disrupting contraction stress at the interface between the composites and tooth, and can be transferred to the tooth structure. In order for the composite/tooth interfacial bond strength to overcome the detrimental shrinkage stress, many approaches such as the development of low shrinkage monomer/composite materials, better bonding agents with improved bonding strength & sealing capability, and various curing and placement techniques aiming to relieve the shrinkage stress by flow have been proposed and investigated.

For the past several decades, there are extensive investigations from both academics and industries to design dental composite with low polymerization shrinkage and shrinkage stress. A variety of different resin and filler system have been studied, yet to date 2,2-bis[4-(2-hydroxy-3-methacryloxy-prop-1-oxy)phenyl]propane (Bis-GMA), Bis-GMA derivative such as ethoxylated Bis-GMA (or EBPADMA), and urethane dimethacrylate (such as 1,6-bis(methacryloxy-2-ethoxycarbonylamino)-2,4,4-trimethylhexane) based oligomers/monomers are still the predominantly used structural dental resin. There is still significant interest to develop dental resin and composite with reduced shrinkage stress. This is highly demanding mission as shrinkage stress generation and control is affected by multiple factors and requires intense research efforts to develop novel dental composites with significantly decreased shrinkage stress, without compromising strength, modulus, and a variety of other key properties.

SUMMARY

A dental restorative composition with reduced shrinkage stress and method of restoring a tooth cavity is disclosed. The composition includes a polymerizable stable radical which in one embodiment is a polymerizable stable radical containing a 2,2,6,6-tetramethylpiperidin-N-oxyl moiety. The composition typically further includes a free radical polymerizable resin, a free radical polymerizable diluent, organic and/or inorganic glass filler system, and photoinitiation system (photoinitiator and co-initiator).

Among the many advantages of exemplary embodiments is that compositions are provided that demonstrate outstanding combinations of excellent mechanical strength, hardness, and flexural modulus, while shrinkage stress caused by polymerization is significantly decreased.

Other features and advantages of the present invention will be apparent from the following more detailed description of exemplary embodiments, taken in conjunction with the accompanying drawings which illustrate, by way of example, the principles of the invention.

DETAILED DESCRIPTION OF EXEMPLARY EMBODIMENTS

Figure 1:
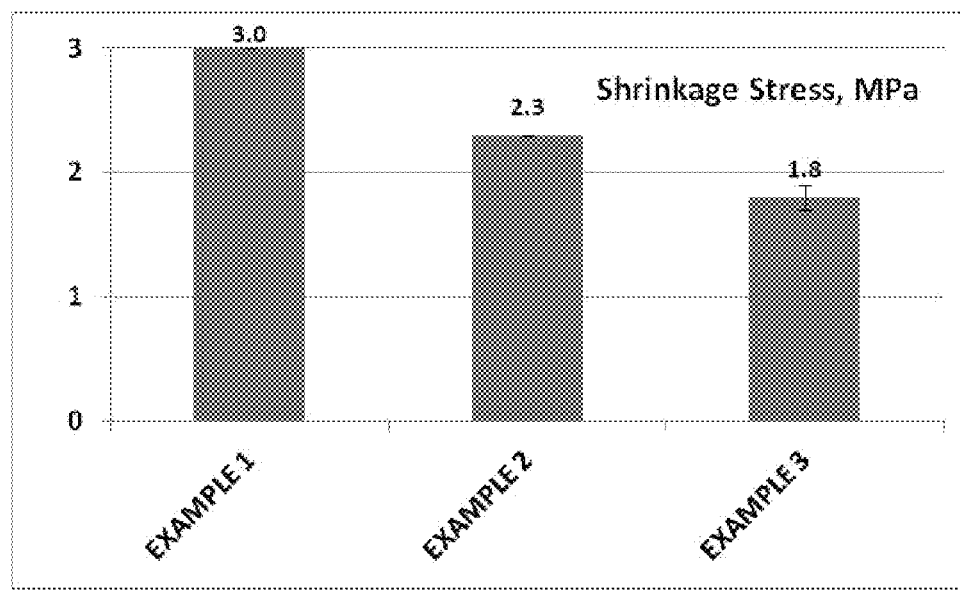
FIG. 1 graphically illustrates measured results of the effect of EGAMA-ATMPO on shrinkage stress at 60 min of examples employing 75.4 wt % filled composite.

Exemplary embodiments are directed dental composite compositions include at least one stable polymerizable radical and which exhibit reduced polymerization stress. The stable radical may be selected from the group consisting of phenothiazine, 2,2-diphenyl-1-picrylhydrazyl radicals, galvinoxyl radicals, triphenylmethyl radicals, and/or (meth) acrylate substituted or unsubstituted 2,2,6,6-tetramethylpiperidinyl-1-oxyl radicals. In certain embodiments, the polymerizable stable radical contains a 2,2,6,6-tetramethyl-piperidin-N-oxyl moiety.

Typically, during the free radical, bulk polymerization of multifunction monomers, the rapid increase of viscosity restricts the mobility of polymer segments, and the subsequent decrease in free volume causes several orders of magnitude decease in the reacting species' mobility. Consequently, a series of phenomena can occur, such as intramolecular cyclization, microgelation, autoacceleration (when termination become reaction-diffusion-controlled), autodeceleration (when chain propagation also becomes diffusion-controlled), and trapped radicals. Due to the efficient photo-curing of modern dental resin/composite, densely crosslinked dimethacrylate networks can form swiftly upon the start of irradiation and the system's viscoelastic properties undergo dramatic transformation (from a viscous paste to a glassy network) within a very short period of time. At the initial stage of photopolymerization of multifunctional (meth)acrylates, a significant portion of pendant methacrylate double bonds are consumed by intramolecular cyclization, subsequently leading to the formation of internally crosslinked microgel and a quite heterogeneous network with very early onset of gelation point. In case of free radically initiated bulk polymerization of dimethacrylates, the experimentally measured macroscopic Gel Point, when the microgels join together to form a continuous network, has been reported to occur at very low double bond conversion—less than 5% for a Bis-EMA system (J. W. Stansbury, Dental Materials, 2012, Vol 28, 13-22).

Therefore, in addition to designing the resin matrix with dramatically different backbone structure, molecular weight, and optimize filler loading/composition, there are potential opportunities to reduce shrinkage stress by mediating the polymerization and network development kinetics. One promising strategy is by delaying gelation and vitrification point. As revealed by simultaneous shrinkage stress~double bond conversion measurements (H. Lu, C. N. Bowman, J. W. Stansbury, Dental Materials, 2004, Vol 20, 979-986; J. W. Stansbury, et al, Dental Materials, 2005, Vol 21, 56-67), it was found that the predominant portion of the shrinkage stress did not start to develop until a much higher extent of polymerization was reached. In these studies, more than 70% of the overall shrinkage stress was observed to develop over the last 15% of conversion. The significant rise of stress over conversion in the latter regime of polymerization is predominately associated with the several orders of magnitude increase of material's elastic modulus during the vitrification stage (J. W. Stansbury, Dental Materials, 2012, Vol 28, 13-22; Steeman P A M, Dias A A, Wienke D, Zwartkruis T, *Macromolecules,* 2004, Vol 37, 7001-7007). Therefore, one pathway for reducing the magnitude of the shrinkage stress could be using the living/controlled radical polymerization chemistry to delay the gelation and vitrification point.

Several major technologies to enable living/controlled radical polymerizations such as atom transfer radical polymerization (ATRP), nitroxide mediated polymerization (NMP), and reversible addition-fragmentation chain transfer (RAFT) polymerization have attracted very intense research activities in the past couple decades. Radical polymerizations which involve a reversible chain transfer step can enable facile pathways to provide living characteristic to free radical polymerization. RAFT polymerization, first reported by Commonwealth Scientific and Industrial Research Organization (CSIRO) scientists in the 1990s, has been successfully used in the synthesis of well-defined homo, gradient, block, comb, star, and hyperbranched polymers (Moad G, Rizzaardo E, Thang S H, Australian Journal of Chemistry 2005, Vol 58, 379-410). RAFT agents based on dithiocarbamates, dithiobenzoates, trithiocarbonates, and xanthates have been developed. Given the appropriate combination of RAFT agent, monomer system, and reaction conditions, RAFT mediated polymerization can be applicable to a range of monomers under a variety of conditions.

Another facile approach to achieve living/controlled radical polymerizations is through nitroxide-mediated radical polymerization. While using various nitroxide as trapping agents to study the free radical polymerization's mechanisms, Dr. David Solomon & co-researchers at CSIRO pioneered the research in the area of living/controlled radical polymerizations and invented nitroxide-mediated radical polymerization (Solomon, D. H.; Rizzardo, E.; Cacioli, P. U.S. Pat. No. 4,581,429, 1986). NMP is a unique and attractive system as it is metal-free (unlike ATRP), relatively effective in a range of monomers, and can bypass certain limitations introduced by mercapto moiety as encountered in most RAFT polymerization. In many cases, nitroxide-mediated radical polymerization can yield odorless and colorless polymers without arduous purification.

U.S. Pat. No. 5,847,025 discloses the use of anaerobic stabilizer and/or stable organic radicals to improve vacuum stability and ambient light stability for dental filling material. Stable organic radical, such as 2,2,6,6-tetramethylpiperidin-1-oxyl (TEMPO) radical, was utilized to decrease the light sensitivity without causing deterioration in bending strength and flexural modulus. U.S. Pat. No. 8,026,295 describes the use of stable radical, preferably comprising a 4-amino-2,2,6,6-tetramethylpiperidin-1-oxyl moiety, to decrease ambient light sensitivity/increase "work time" for light curing dental composition. Drastically improved ambient light stability, tested per ISO-4049 method, has been demonstrated with the compositions comprising the nitroxide stable radical incorporating 4-amino-2,2,6,6-tetramethylpiperidin-1-oxyl moiety, while achieving comparable mechanical strength and flexural modulus. Furthermore, the stable radicals disclosed in this patent could also incorporate methacrylate functional group, therefore can be covalently attached onto polymer during photo-curing and reduce their leachability.

During the nitroxide mediated polymerization, the propagating radicals are reversibly deactivated through reaction with a stable radical (such as 2,2,6,6-tetramethylpiperidinyloxy TEMPO). The utilization of NMP technology in crosslinked polymer has not received extensive studies as compared to the linear, block, or branched polymer system. However, it has been reported that network with more homogenous structure are formed in the controlled/living free radical polymerization (H. Gao, K. Matyjaszewski, Progress in Polymer Science, 2009, Vol 34, 317-350). Recently, a fairly comprehensive model for the copolymerization kinetics in crosslinked vinyl/divinyl systems in the presence of nitroxide mediators has been developed, and validated using experimental data of TEMPO-mediated copolymerization of styrene and divinylbenzene. It was found that the kinetic rate constant for primary cyclization in TEMPO-mediated system is lower than conventional copolymerization and the kinetic chain length is shorter, both reduced primary cyclization and kinetic chain length can lead to more homogeneous network (J. C. Hernandez-Ortiz et al, Macromolecular Reaction Engineering, 2009, Vol 3, 288-311).

Moreover, the study also found that the gelation point was significantly delayed in the TEMPO-mediated system as compared to conventional free radical copolymerization system. In the conventional monovinyl/divinyl copolymerization initiated by BPO, the gelation point was reached at about 1.2% monomer conversion; whereas in TEMPO mediated system, with the same initiator, the gelation point wasn't reached until approximately 58% monomer conversion (J. C. Hernandez-Ortiz et al, Macromolecular Reaction Engineering, 2009, Vol 3, 288-311). The impact of nitroxide on "living" radical network polymerization was also studied by G. V. Korolev et at (G. V. Korolev et al, Polymer Science, Ser A, 2001, Vol 43, 482-289) in a crosslinked styrene/dimethacrylate system, and it was found the onset of gelation was shifted to much higher degree of polymerization (>10%) as compared to the control network without nitroxide (<3%). E. Tuinman et at also investigated the TEMPO-mediated, bulk polymerization of styrene and divinylbenzene initiated by BPO, therefore a bimolecular NMRP—Nitroxide Medicated Radical Polymerization, without using a TEMPO-capped prepolymer in the initial mixture. It was found that in the TEMPO-mediated styrene/divinylbene copolymerization system, the gelation point was significantly delayed from around 7% to 50% monomer conversion, as compared to the control system without TEMPO (G E. Tuinman et al, Journal of Macromolecular Science, Part A, 2006, Vol 43, 995-1011). In case of free radically initiated bulk polymerization of dimethacrylates, the experimentally measured macroscopic Gel Point, when the microgels join together to form a continuous network, has been reported to occur at very low double bond conversion—approximately 5% (C. S. Pfeifer, N. D. Wilson, Z. R. Shelton, J. W. Stansbury; Polymer 2011, Vol 52, 3295-3303). Whereas in nitroxide mediated polymerization, the rapid chain propagating process can be mediated by nitroxide radical resulting in shorter kinetic chain length being formed, hence the conversion at onset of autoacceleration where termination becomes reaction-diffusion controlled can be delayed, resulting in gelation point occurred at later conversion. Although nitroxide compound has been used to achieve living/controlled radical polymerization, the use of nitroxide-mediated approach to reduce shrinkage stress in dental resins and composites has not been reported before.

Disclosed herein is a method to reduce polymerization shrinkage stress in crosslinked polymer, such as dental composites, by utilizing the composition containing the polymerizable stable radical. The polymerizable stable radical is highly beneficial to the biocompatibility of the composition as it can be covalently attached onto polymer during polymerization and reduce their leachability. Polymerizable stable radicals that contribute to decreased polymerization shrinkage stress include but are not limited to stable radical that contain 2,2,6,6-tetramethylpiperidin-N-oxyl moiety, such as compounds shown below:

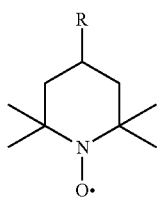

in which R=X(Y$_1$,Y$_2$,Y$_3$)Z;

wherein X, when present, is N, O, S, C—O, C—O—O, S—O, S—O—O, P—O, P—O—O, or P—O—O—O;

wherein Y$_1$, Y$_2$, and Y$_3$ are independently, when present, aryl or substituted aryl, linear or branched alkyl or arylalkyl;

and wherein Z, independently, is an unsaturated functional group.

For example, the linear or branched groups for Y$_1$, Y$_2$, and Y$_3$ may be (CH$_2$)$_n$; (CH$_2$CH$_2$O)$_n$; or (CH$_2$CHCH$_3$O)$_n$; in which n=0-20. Examples of the unsaturated group Z include, but are not limited to, vinyl, acrylamide, methacrylamide, acrylate, and methacrylate.

In its most complex form, the stable polymerizable radical having a 2,2,6,6-tetramethylpiperidin-N-oxyl moiety may be of the following structure:

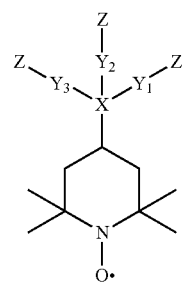

In a simple form, the compound has the structure:

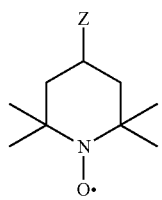

Examples of specific compounds encompassed by the disclosed general structure include, but are not limited to the following, which may be used individually or in combination:

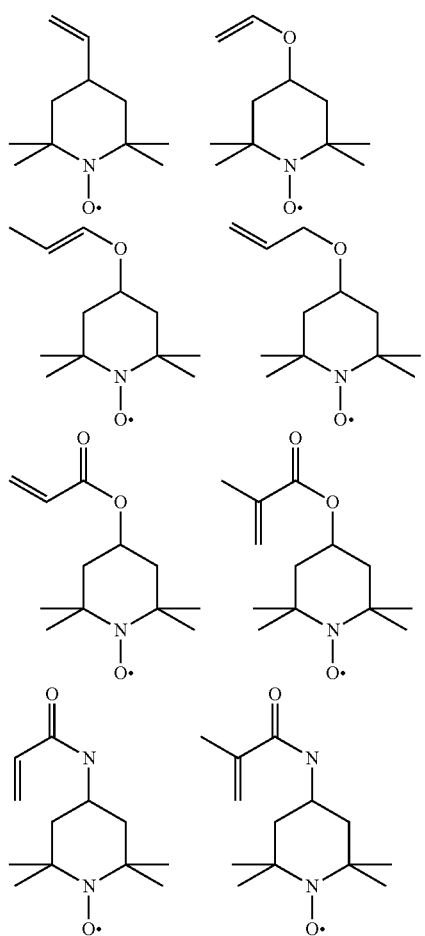

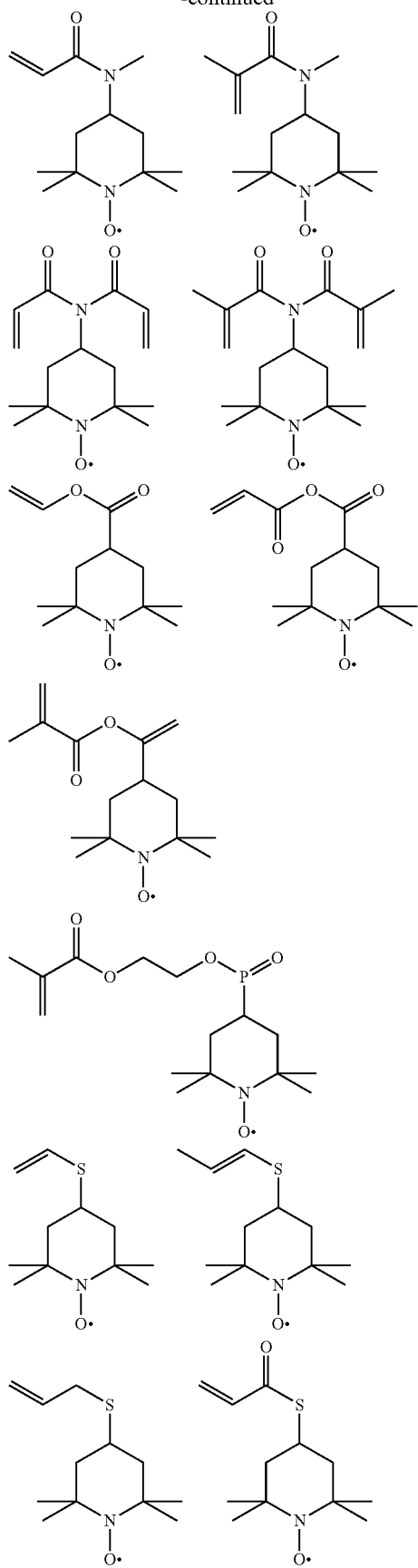
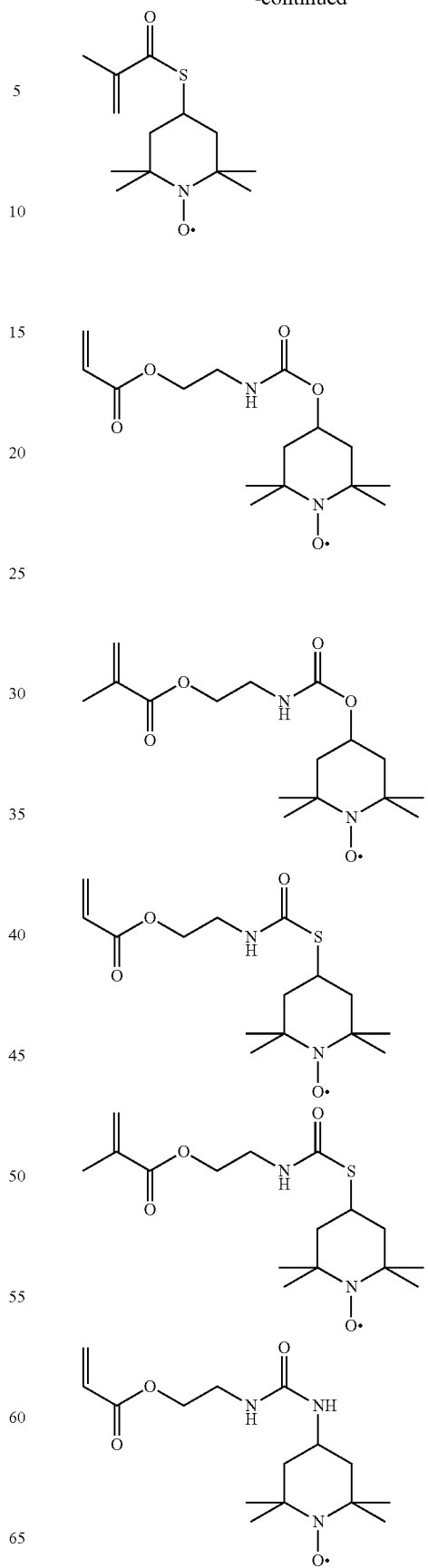

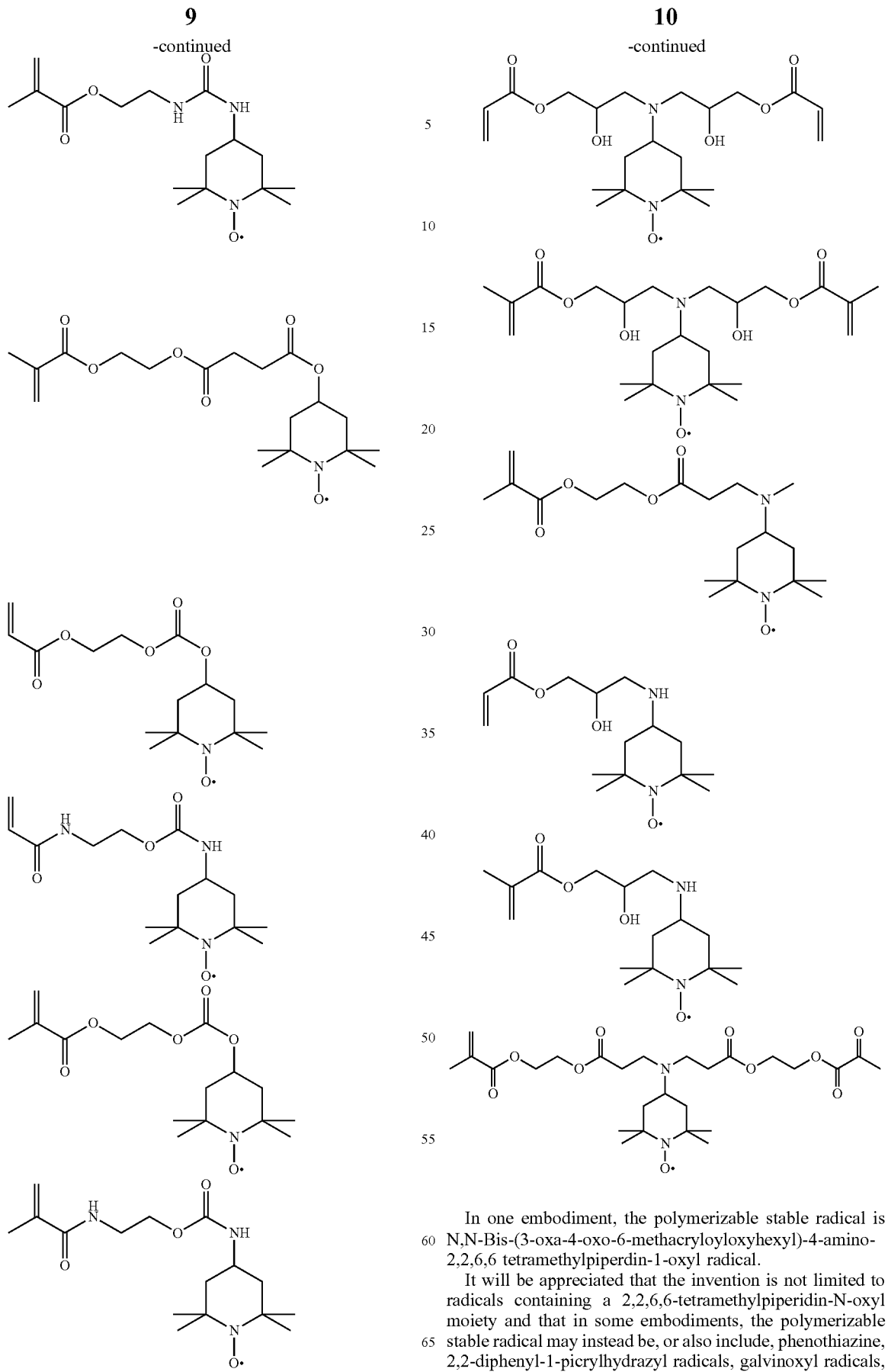

In one embodiment, the polymerizable stable radical is N,N-Bis-(3-oxa-4-oxo-6-methacryloyloxyhexyl)-4-amino-2,2,6,6 tetramethylpiperdin-1-oxyl radical.

It will be appreciated that the invention is not limited to radicals containing a 2,2,6,6-tetramethylpiperidin-N-oxyl moiety and that in some embodiments, the polymerizable stable radical may instead be, or also include, phenothiazine, 2,2-diphenyl-1-picrylhydrazyl radicals, galvinoxyl radicals, triphenylmethyl radicals and combinations thereof.

The polymerizable stable radicals may be incorporated in any amount sufficient to reduce shrinkage stress but at sufficiently low levels that do not also compromise the mechanical performance of the cure composite. In some embodiments, the polymerizable stable radical is present from about 0.005% by weight of the restorative composition up to about 5% by weight, in some cases from about 0.015% by weight up to about 3% by weight, such as about 0.03% by weight up to about 1% by weight in other cases.

The polymerizable stable radical are added to form compositions, such as dental restorative compositions, that provide reduced shrinkage stress during polymerization. The composition in the described invention also has good mechanical properties and it can be cured by traditional quartz-tungsten-halogen (QTH) dental lamp, or light emitting diode (LED) dental lamp, or plasma arc curing (PAC) dental lamp.

In addition to the polymerizable stable radical, the composition includes a polymerizable resin, typically one or more (meth)acrylate monomers/oligomers. The polymerizable (meth)acrylate monomer/oligomer may be a free radically polymerizable compound.

Exemplary free radically polymerizable resin compounds include, for example, mono-, di- or multi-methacrylates and acrylates such as 2,2-bis[4-(2-hydroxy-3-methacryloyloxy-propoxy)phenyl]propane (Bis-GMA), 1,6-bis(2-methacryloxyethoxycarbonylamino)-2,4,4-trimethylhexane (UDMA), 2,2-bis[4-(methacryloyloxy-ethoxy)phenyl]propane (or ethoxylated bisphenol A-dimethacrylate) (EB-PADMA), isopropyl methacrylate, triethyleneglycol dimethacrylate, diethyleneglycol dimethacrylate, tetraethyleneglycol dimethacrylate, 3-(acryloyloxy)-2-hydroxypropyl methacrylate, 1,3-propanediol dimethacrylate, 1,6-hexanediol di(meth)acrylate, 1,12-dodecanediol dimethacrylate, pentaerythritol triacrylate, pentaerythritol tetraacrylate, pentaerythritol tetramethacrylate.

The polymerizable (meth)acrylate monomer/oligomer or other free radically polymerizable resin may be present in the composition in an amount of from about 5 weight percent to about 80 weight percent of the composite composition, such as from about 10 weight percent to about 50 weight percent or from about 15 weight percent to about 40 weight percent of the composite composition.

The dental restorative composition disclosed herein further comprises one or more types of filler particles that are suitable for use in dental compositions. Fillers that are suitable for use in the composition described herein can provide desired physical and curing properties, such as increased mechanical strength, modulus, hardness, wear resistance, reduced thermal expansion, and polymerization volumetric shrinkage.

Examples of suitable filler particles include, but are not limited to, strontium borosilicate, strontium fluoroalumino borosilicate glass, strontium alumino sodium fluoro phosphor-silicate glass, barium borosilicate, barium fluoroalumino borosilicate glass, barium aluminum-borosilicate glass, barium alumino borosilicate, calcium alumino sodium fluoro silicate, lanthanum silicate, lanthanum aluminosilicate, calcium alumino sodium fluoro phosphor silicate, and the combination comprising at least one of the foregoing fillers. Filler particles can further comprise silicon nitrides, titanium dioxide, fumed silica, colloidal silica, quartz, kaolin ceramics, calcium hydroxy apatite, zirconia, and mixtures thereof. Examples of fumed silica include OX-50 from DeGussa AG (having an average particle size of 40 nm), Aerosil R-972 from DeGussa AG (having an average particle size of 16 nm), Aerosil 9200 from DeGussa AG (having an average particle size of 20 nm), other Aerosil fumed silica may include Aerosil 90, Aerosil 150, Aerosil 200, Aerosil 300, Aerosil 380, Aerosil R711, Aerosil R7200, and Aerosil R8200, and Cab-O-Sil M5, Cab-O-Sil TS-720, Cab-O-Sil TS-610 from Cabot Corp.

Fillers are present in amounts of from about 50 weight percent to about 90 weight percent of the composite composition, such as from about 60 weight percent to about 85 weight percent or from about 70 weight percent to about 80 weight percent of the composite composition. The filler particles can have a particle size of from about 0.002 microns to about 25 microns. In one embodiment, the filler can comprise a mixture of a micron-sized radiopaque filler such as barium alumino fluoro borosilicate glass (BAFG, having an average particle size of about 1 micron) with nanofiller particles, such as fumed silica such as OX-50 from Degussa AG (having an average particle size of about 40 nm). The concentration of micron-size glass particles can range from about 70 weight percent to about 80 weight percent of the nitroxide-mediated composition, and the nano-size filler particles can range from about 1 weight percent to about 10 weight percent of the composite composition.

The filler particles used in the composition disclosed herein may be surface treated before they are blended with organic compounds. Surface treatment using silane coupling agents or other compounds may be beneficial as it enables the filler particles to be more uniformly dispersed in the organic resin matrix and improve physical and mechanical properties. Suitable silane coupling agents include 3-methacryloxypropyltrimethoxysilane, 3-acryloxypropyltrimethoxysilane, 3-glycidoxypropyltrimethoxysilane, 3-mercaptopropyltrimethoxysilane, and mixtures thereof.

The dental restorative composition described herein further contains a polymerization initiator system. The initiator is not particularly limited and may be a photoinitiator and preferably one effective in the visible light spectrum range suited for dental restorative applications, such as diketone type initiator camphorquinone (CQ), derivative of diketone initiator, and acylphosphine oxide type photoinitiator such as diphenyl (2,4,6-trimethylbenzoyl) phosphine oxide (L-TPO), and combinations thereof. Other diketone type photoinitiator such as 1-phenyl-1,2 propanedione (PPD), and acylphosphine oxide type photoinitiator such as bis(2, 4,6-trimethylbenzoyl)-phenylphosphine oxide (Irgacure 819), ethyl 2,4,6-trimethylbenzylphenyl phosphinate (Lucirin LR8893X), may also be used. The polymerization photoinitiator or combination is present in an amount of from about 0.05 weight percent to about 1.00 weight percent, such as from about 0.08 weight percent to about 0.50 weight percent or from about 0.10 weight percent to about 0.25 weight percent of the nitroxide-mediated composition. Using such a small amount of a polymerization photoinitiator decreases the potential discoloration of the composition. By contrast, compositions containing a high concentration of photoinitiator are more likely to be discolored.

The polymerization initiator system of the dental restorative compositions described herein may further include a polymerization accelerator, which may be a tertiary amine. One example of a suitable tertiary amine is ethyl 4-(dimethylamino)benzoate (EDAB). Other tertiary amines that may be used include 2-(ethylhexyl)-4-(N,N-dimethylamino) benzoate, 4-(Dimethylamino) benzonitrile, and the like. The polymerization accelerator may be present in an amount of from about 0.03 weight percent to about 0.18 weight percent of the dental restorative composition, such as from about 0.04 weight percent to about 0.15 weight percent or from about 0.05 weight percent to about 0.12 weight percent of the dental restorative composition. The compositions disclosed herein are capable of being activated by a curing light having a wavelength of from about 360 nm to about 520 nm.

The dental restorative compositions described herein may further include additives in order to provide specifically desired features. These additives include ultra-violet stabilizers, fluorescent agents, opalescent agents, pigments, viscosity modifiers, fluoride-releasing agents, polymerization inhibitors, and the like. Typical polymerization inhibitors for a free radical system may include hydroquinine monomethyl ether (MEHQ), butylated hydroxytoluene (BHT), tertiary butyl hydro quinine (TBHQ), hydroquinone, phenol, and the like. The polymerization inhibitors may be present in amounts of from about 0.001 weight percent to about 1.5 weight percent of the dental restorative composition, such as from about 0.005 weight percent to about 1.1 weight percent or from about 0.01 weight percent to about 0.08 weight percent of the dental restorative composition. The composition may also include one or more polymerization inhibitors.

The dental restorative composition disclosed herein may be made by any known and conventional method. In embodiments, the composition is made by mixing the components together at a temperature of from about 20° C. to about 60° C., such as from about 23° C. to about 50° C. The monomers, photoinitiators, accelerators, and other additives can be blended in a double planetary mixer (such as Ross Mixer) that is equipped with temperature and vacuum control, for a time of from about 20 minutes to an hour, such as from about 30 minutes to 50 minutes, under from about 20 to about 27 inches Hg vacuum at room temperature (from about 23° C. to about 27° C.) or further mixing in the Ross Mixer takes place for a time of from about 10 minutes to about 30 minutes, such as from about 15 minutes to about 25 minutes, under from about 20 to about 27 inches Hg vacuum at an elevated temperature of from about 40° C. to about 60° C. In alternative embodiments, the paste may be mixed on a high intensity mixer such as Resodyn Acoustic Mixer for a time of from about 30 minutes to about 60 minutes, such as from about 35 minutes to about 55 minutes or about 45 minutes under from about 20 to about 27 inches Hg vacuum at a temperature of from about 18° C. to about 30° C., such as 20° C. to about 27° C. or 23° C.

EXAMPLES

The invention is further described by way of the following examples, which are presented by way of illustration, not of limitation. Unless otherwise indicated, all parts and percentages are by weight.

Reference is made to the following components used in describing the examples:

Resin Blend-1: a blend of 2,2-bis[4-(2-hydroxy-3-methacryloxyprop-1-oxy)phenyl]propane (Bis-GMA), 1,6-bis(2-methacryloxyethoxycarbonylamino)-2,4,4-trimethylhexane (UDMA), and triethylene glycol dimethacrylate (TEGMDA);

Resin Blend-2: a blend of UDMA and TEGMDA;

EGAMA-ATMPO: N,N-Bis-(3-oxa-4-oxo-6-methacryloyloxyhexyl)-4-amino-2,2,6,6 tetramethylpiperdin-1-oxyl radical;

CQ: Camphorquinone;

EDAB: Ethyl 4-dimethylaminobenzoate;

BHT: Butylated hydroxytoluene;

Silanated BABG-1: barium alumino borosilicate glass surface treated by γ-methacryloxypropyltrimethoxysilane and having a refractive index of 1.55;

Silanated BFBG-1: barium fluoroalumino borosilicate glass surface treated by γ-methacryloxypropyltrimethoxysilane and having a refractive index of 1.53;

Silanated BFBG-2: barium fluoroalumino borosilicate glass surface treated by γ-methacryloxypropyltrimethoxysilane and having a refractive index of 1.51;

Silanated SAFG-1: Silanated strontium-alumino sodium-fluoro-phosphorsilicate glass surface treated by γ-methacryloxypropyltrimethoxysilane and having a refractive index of 1.51.

Example 1

In Example 1, a dental restorative composition having 75.4% by weight filler was prepared by adding 49.61 parts silanated BABG-1, 24.81 parts silanated BFBG-1, and 0.98 parts of fumed silica (Aerosil R-972) to an activated resin blend consisting of 24.18 parts of Resin Blend-1, 0.04 parts of CQ, 0.07 parts of EDAB, 0.01 parts of BHT, 0.25 parts UV absorber (Univul M40), and 0.05 parts of a fluorescent agent (flublau concentrate).

Example 2

A second example was created in the same manner as Example 1, except that a polymerizable stable radical (EGAMA-ATMPO) was added to the composition, with 49.61 parts silanated BABG-1, 24.81 parts silanated BFBG-1, and 0.98 parts of Aerosil R-972 added to activated an resin blend consisting of 24.08 parts of Resin Blend-1, 0.04 parts of CQ, 0.07 parts of EDAB, 0.01 parts of BHT, 0.25 parts of Univul M40, 0.05 parts of flublau concentrate, and 0.10 parts of EGAMA-ATMPO.

Example 3

A third example dental restorative composition was prepared, this time by adding 49.61 parts silanated BABG-1, 24.81 parts silanated BFBG-1, and 0.98 parts of Aerosil R-972 to an activated resin blend consisting of 23.88 parts of Resin Blend-1, 0.04 parts of CQ, 0.07 parts of EDAB, 0.01 parts of BHT, 0.25 parts of Univul M40, 0.05 parts of flublau concentrate, and 0.30 parts of EGAMA-ATMPO.

Examples 1 through 3 were analyzed to assess shrinkage, including shrinkage stress and volumetric shrinkage, as well as to assess mechanical properties including flexural strength, flexural modulus, and fracture toughness.

Shrinkage Stress:

Shrinkage stress was measured with a shrinkage stress measurement device, referred to as a tensometer, designed and fabricated at the Paffenbarger Research Center of the American Dental Association Foundation (ADAF). This device is based on the cantilever beam theory that bending force generated by a shrinking sample during polymerization causes the cantilever beam to deflect. Polished top and bottom quartz rods (6.0 mm in diameter) were silanated with two layers of 2 vol % γ-methacryloxypropyltrimethoxysilane/acetone solution. Dental resin or composite are injected into a cell between two glass rods with 6.0 mm in diameter and 2.25 mm in thickness. The material is cured with a QHL-75 halogen lamp at a light intensity of 400 mW/cm$^2$ for sixty seconds. A more detailed description, experimental procedure, and characterization of the tensometer are discussed in (H. Lu et al., Journal of Materials Science, Materials in Medicine, 2004, Vol. 15, 1097-1103), which is hereby incorporated by reference in its entirety.

Volumetric Shrinkage:

The densities of uncured and twenty four hour post-cured restorative materials were determined by Helium Pycnometer (MicroMeritics AccuPycII 1340) at 25° C. Cured composite specimens, 10 mm in diameter×2.5 mm in thickness, were prepared by curing the composite in a stainless steel mold with Spectrum 800 at an intensity of 550 mW/cm$^2$ for sixty seconds. The cured specimen was stored at room temperature for twenty four hours prior to the measurements. The densities of cured and uncured composites were used to calculate polymerization shrinkage. The volume shrinkage was calculated as:

% Volume Shrinkage=(Density$_{cured}$−Density$_{uncured}$)/Density$_{cured}$×100

Flexural Strength and Flexural Modulus:

Specimens for 3-point bending flexural test were prepared according to ISO 4049. Sample were filled into 25 mm×2 mm×2 mm stainless steel mold, then covered with Mylar film and cured using Spectrum 800 (DENTSPLY Caulk) halogen lamp at intensity of 550 mW/cm$^2$ for 4×20 seconds uniformly across the entire length of the specimen. The set specimens were stored in deionized water at 37° C. for 24 hours prior to the test. Flexural test was conducted using an Instron Universal Tester Model 4400R with crosshead speed 0.75 mm/min under compressive loading mode.

Fracture Toughness:

To measure fracture toughness, samples were filled into 25 mm×5 mm×2 mm stainless steel molds, then covered by Mylar film and cured using Spectrum 800 lamp at intensity of 550 mW/cm$^2$ from both sides. After storage in DI-water at 37° C. for 24-hour, a notch (depth 2.4 mm, width 0.4 mm) was placed in the center of the specimen using a diamond cutting disc and the exact notch depth was measured with a microscope. Fracture toughness specimens were then fractured on Instron 3366 under 3-point bending mode at crosshead speed of 0.5 mm/min.

A summary of the results obtained for Examples 1 through 3 are shown in Table 1:

TABLE 1

| Effect of EGAMA-ATMPO on 75.4 wt % Filled Composite | | | |
| --- | --- | --- | --- |
| Example Composite | EXAMPLE 1 | EXAMPLE 2 | EXAMPLE 3 |
| EGAMA-ATMPO wt % in EXAMPLE | 0 | 0.1 | 0.3 |
| Filler Loading, wt % | 75.4 | 75.4 | 75.4 |
| Shrinkage Stress, MPa (s.d.) | 3.0 (0) | 2.3 (0) | 1.8 (0.1) |
| Volumetric Shrinkage, % (s.d.) | 3.0 (0.2) | 3.0 (0.1) | 3.3 (0.1) |
| Flexural Strength, MPa (s.d.) | 136 (12) | 147 (22) | 141 (18) |
| Flexural Modulus, MPa (s.d.) | 10034 (525) | 9740 314) | 9495 (354) |
| Fracture Toughness, MPa*m$^{1/2}$ (s.d.) | 2.5 (0.1) | 2.5 (0.1) | 2.4 (0.1) |

Figure 2:
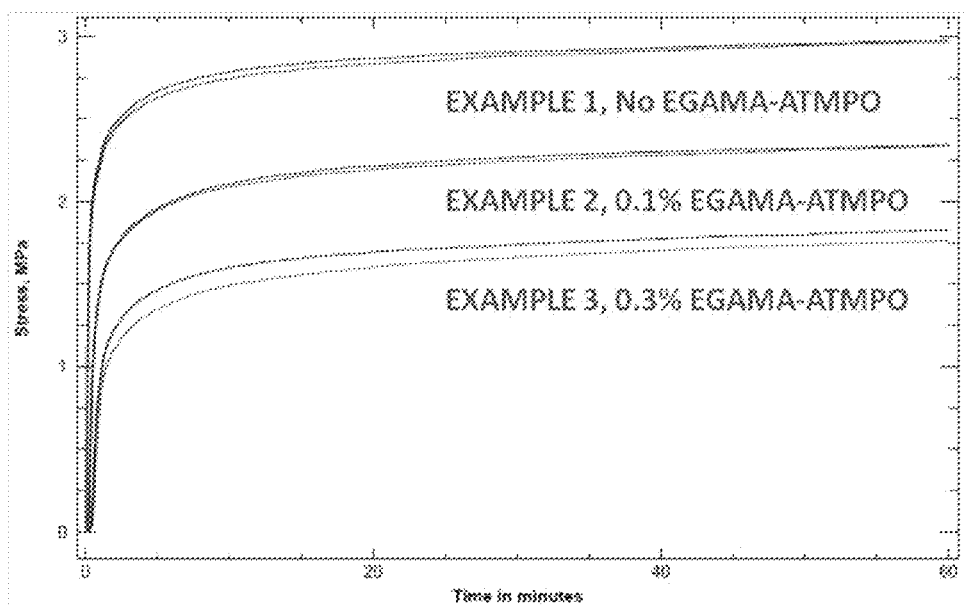
FIG. 2 graphically illustrates measured results of the effect of EGAMA-ATMPO on shrinkage stress as a function of time for examples containing 75.4 wt % filled composite.
Figure 3:
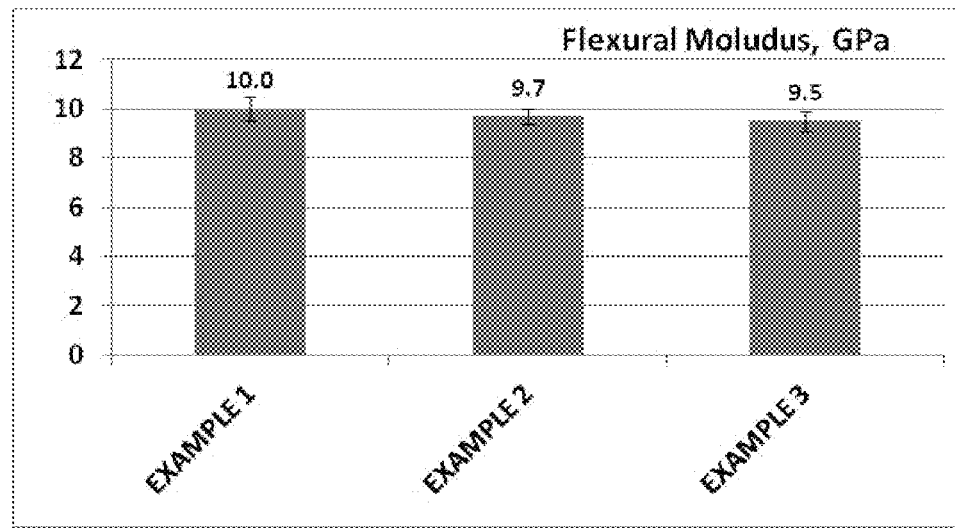
FIG. 3 graphically illustrates measured results of the effect of EGAMA-ATMPO on flexural modulus of examples of a 75.4 wt % filled composite.
Figure 4:
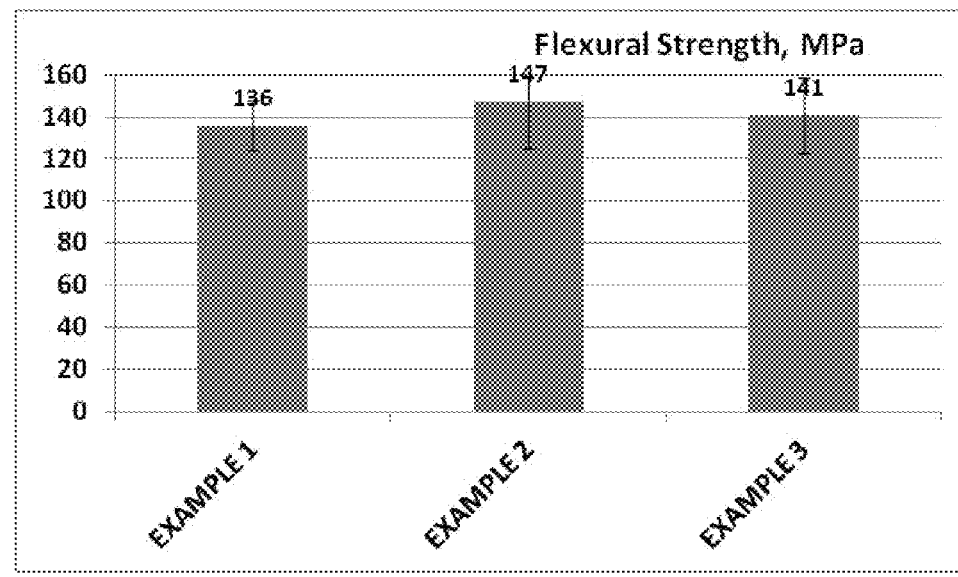
FIG. 4 graphically illustrates measured results of the effect of EGAMA-ATMPO on flexural strength of examples of a 75.4 wt % filled composite.

FIGS. 1 through 4 graphically illustrate the determined properties. As illustrated in FIG. 1 and FIG. 2, significant reduction of shrinkage stress was observed comparing control composite of Example 1 in which no polymerizable stable radical was present and demonstrated 3.0 MPa stress to Example 2 with 0.1% by weight polymerizable stable radical (2.3 MPa stress) and Example 3 with 0.3% by weight polymerizable stable radical (1.8 MPa stress). Moreover, within the range of concentrations of stable radical studied (from 0.1 wt % to 0.3 wt % in total paste), no appreciable decrease in flexural strength, flexural modulus, and fracture toughness can be found, as shown in FIG. 3 and FIG. 4. The substantial reduction of the material's polymerization stress (a 40% reduction comparing Example 3 vs. Example 1) while still having comparable modulus and strength demonstrates a desirable combination that can enhance long term performance of the restoration.

Another set of examples was created to form a composite having 80% by weight filler.

Example 4

In Example 4, a dental restorative composition was prepared by adding 51.746 parts of silanated BFBG-2, 26.841 parts of silanated SAFG-1, and 1.413 parts of fumed oxide (OX-50) to an activated resin blend consisting of 19.902 parts of Resin Blend-2, 0.033 parts of CQ, 0.060 parts of EDAB, and 0.005 parts of BHT.

Example 5

The dental restorative composition for Example 5 was prepared by again adding 51.746 parts of silanated BFBG-2, 26.841 parts of silanated SAFG-1, and 1.413 parts of OX-50 this time to an activated resin blend consisting of 19.886 parts of Resin Blend-2, 0.033 parts of CQ, 0.060 parts of EDAB, 0.005 parts of BHT, and 0.016 parts of EGAMA-ATMPO.

Example 6

Example 6 was prepared in the same manner, but with 51.746 parts of silanated BFBG-2, 26.841 parts of silanated SAFG-1, and 1.413 parts of OX-50 added to an activated resin blend consisting of 19.872 parts of Resin Blend-2, 0.033 parts of CQ, 0.060 parts of EDAB, 0.005 parts of BHT, and 0.030 parts of EGAMA-ATMPO.

Example 7

In Example 7, a dental restorative composition was prepared by adding 51.746 parts of silanated BFBG-2, 26.841 parts of silanated SAFG-1, and 1.413 parts of OX-50 to an activated resin blend consisting of 19.842 parts of Resin Blend-2, 0.033 parts of CQ, 0.060 parts of EDAB, 0.005 parts of BHT, and 0.060 parts of EGAMA-ATMPO.

Shrinkage and mechanical property tests were conducted on Examples 4 through 7 in the same manner as for Examples 1 through 3. Additionally, these examples were also subjected to a 3-body wear resistance test. Results are shown in Table 2.

3-Body Wear Resistance:

Three-body localized wear resistance is tested according to DENTSPLY/Caulk internal testing method SOP 762-014 (In-Vitro Wear-Testing Method and Apparatus), adopted from University of Alabama-Birmingham (UAB) Leinfelder 3-Body Wear Testing Method (K. Leinfelder, S. Suzuki, Journal of American Dental Association, 1999, Vol 130, 1347-1353). HG-5 polymer was used as food with stainless steel tip. 7.8 kgf (76.5 N) load was used to simulate masticatory force on wear resistance of restorative materials. 400,000 cycles of wear for each specimen was conducted.

TABLE 2

Effect of EGAMA-ATMPO on 80.0% Filled Composite

| Example Composite | EXAMPLE 4 | EXAMPLE 5 | EXAMPLE 6 | EXAMPLE 7 |
|---|---|---|---|---|
| EGAMA-ATMPO wt % in EXAMPLE | 0 | 0.016 | 0.03 | 0.06 |
| Filler Loading, wt % | 80.0 | 80.0 | 80.0 | 80.0 |
| Shrinkage Stress, MPa (s.d.) | 2.6 (0.2) | 2.3 (0.1) | 2.2 (0.2) | 1.8 (0.1) |
| Flexural Strength, MPa (s.d.) | 151 (5) | 166 (3) | 155 (3) | 154 (6) |
| Flexural Modulus, MPa (s.d.) | 11047 (449) | 11295 (379) | 10554 (456) | 10299 (331) |
| Fracture Toughness, MPa*m$^{1/2}$ (s.d.) | 2.75 (0.10) | 2.69 (0.18) | 2.46 (0.12) | 2.45 (0.16) |
| Barcol Hardness | 79 | 80 | 81 | 81 |
| Volumetric Shrinkage, % (s.d.) | 2.22 (0.01) | 2.12 (0.15) | 2.14 (0.24) | 2.32 (0.25) |
| 3-Body Wear Volume Loss, mm (s.d.) | 0.0307 (0.0086) | 0.0274 (0.0044) | 0.0297 (0.0097) | 0.0259 (0.0045) |

Figure 5:
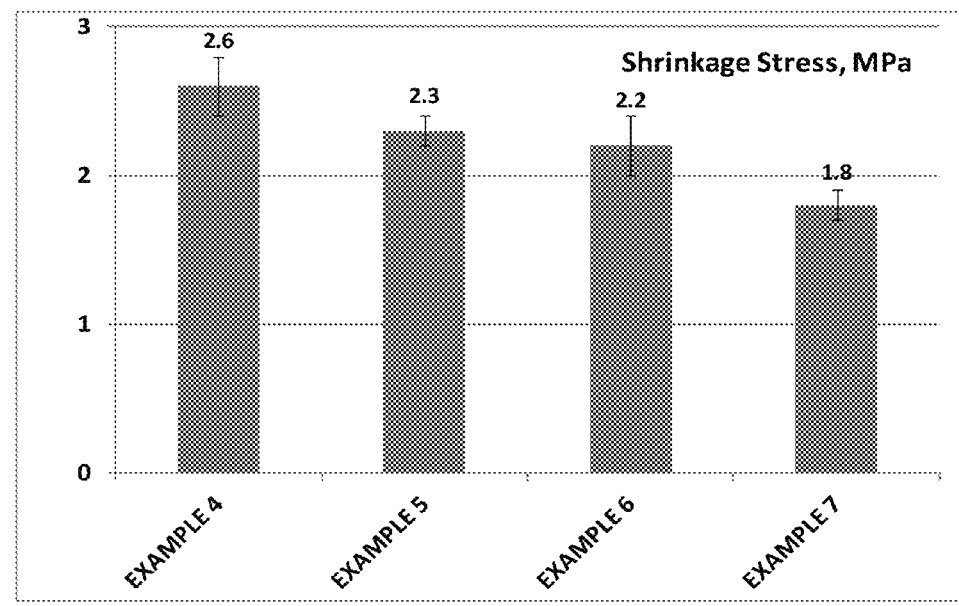
FIG. 5 graphically illustrates measured results of the effect of EGAMA-ATMPO on shrinkage stress of examples employing a 80.0 wt % filled composite.
Figure 6:
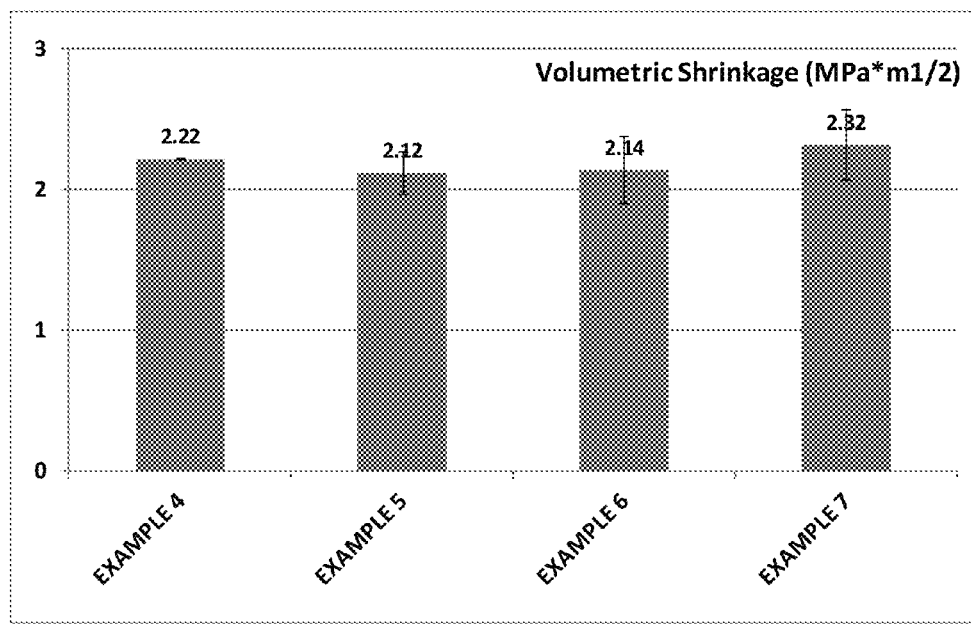
FIG. 6 graphically illustrates measured results of the effect of EGAMA-ATMPO on volumetric shrinkage of examples employing a 80.0 wt % filled composite.
Figure 7:
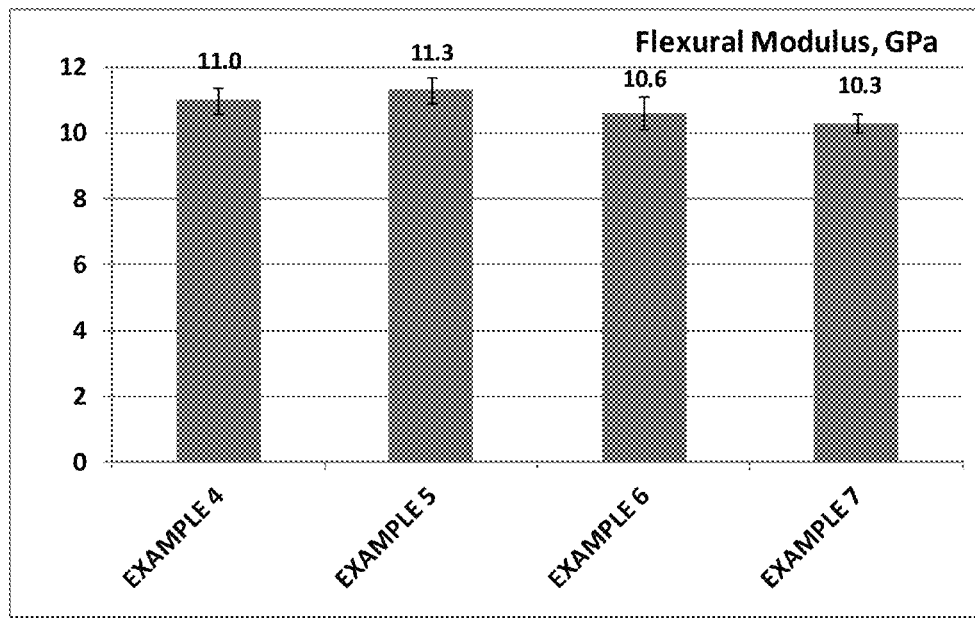
FIG. 7 graphically illustrates measured results of the effect of EGAMA-ATMPO on flexural modulus of examples employing a 80.0 wt % filled composite.
Figure 8:
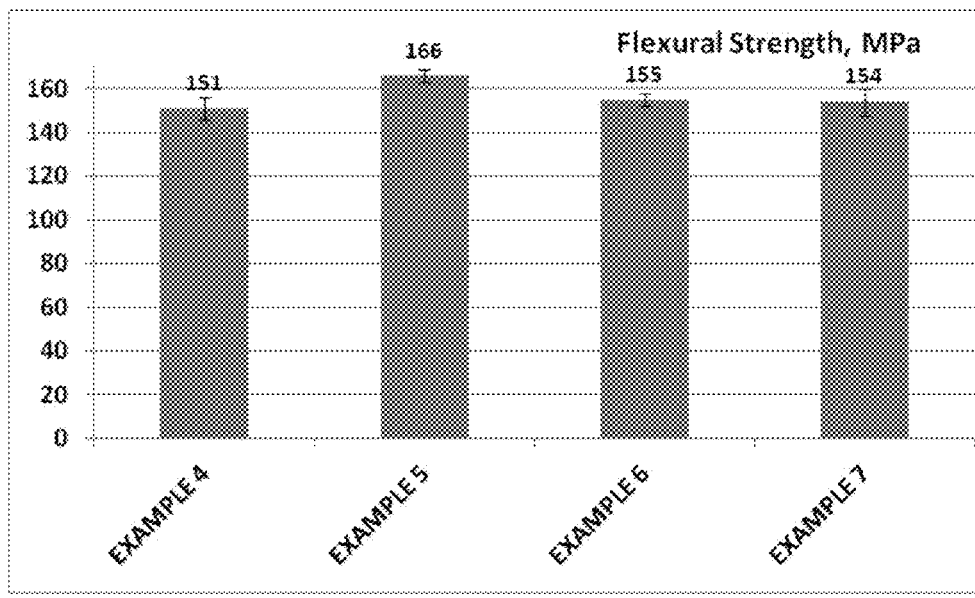
FIG. 8 graphically illustrates measured results of the effect of EGAMA-ATMPO on flexural strength of examples employing a 80.0 wt % filled composite.
Figure 9:
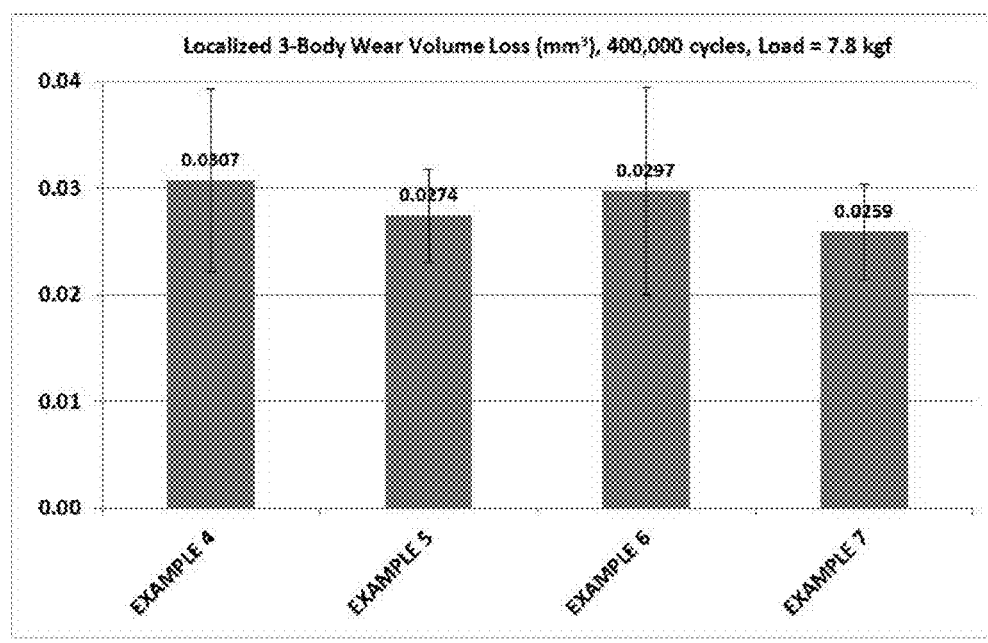
FIG. 9 graphically illustrates measured results of the effect of EGAMA-ATMPO on 3-body wear resistance of examples employing a 80.0 wt % filled composite.

In this set of examples, employing a different resin matrix system and higher filler loading (80 wt %), the impact of EGAMA-ATMPO on shrinkage stress, polymerization shrinkage, and mechanical properties also demonstrated the same surprising and unexpected as the first set of examples. As demonstrated in FIGS. 5 and 6, a steady reduction of shrinkage stress, from 2.6 MPa to 1.8 MPa, is achieved when the concentration of EGAMA-ATMPO was increased from 0.016 wt % to 0.06 wt %. No significant differences for polymerization shrinkage were observed, indicating similar level of curing was achieved. This is further demonstrated by the almost same amount of flexural modulus (FIG. 7), flexural strength achieved (FIG. 8), and not compromising composites' 3-body wear resistance (FIG. 9).

In many cases, bonding between tooth and composite restoration can be weakened by shrinkage stress, which might lead to post-operative sensitivity, microleakage, and even recurrent caries. The significant reduction of shrinkage stress achieved with embodiments of the present invention, while at the same time not reflecting any compromise in the composites' modulus, fracture toughness, and mechanical strength, is quite beneficial to generate dental restoration with not only decreased internal stress, but also reduced interfacial stress applied onto the composite-tooth interface, therefore contribute to improved quality and longevity of restoration.

The compositions of this invention demonstrating outstanding combinations of excellent mechanical strength, hardness, and flexural modulus, while shrinkage stress caused by polymerization can be significantly decreased. The performance of these polymerizable stable radical are remarkable and unexpected, in that they are able to achieve significant shrinkage stress reduction, while not compromising mechanical strength, modulus, fracture toughness, and wear resistance. This unique combination is not met by known conventional inhibitor or stabilizer addition.

It will be appreciated that various of the above-disclosed compositions and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

We claim:

1. A dental composite composition comprising a free-radically polymerizable (meth)acrylate resin, 75 percent by weight or greater of filler particles, and about 0.005 percent to about 5 percent by weight of at least one polymerizable stable radical, the dental composite composition having a flexural modulus after polymerization of about 9500 MPa or greater;
   wherein the polymerizable stable radical reduces shrinkage stress of the dental composite composition caused by polymerization by 10% or greater.

2. The dental composite composition of claim 1, wherein the polymerizable stable radical is selected from the group consisting of phenothiazine, 2,2-diphenyl-1-picrylhydrazyl radicals, galvinoxyl radicals, triphenylmethyl radicals, and (meth)acrylate substituted or unsubstituted 2,2,6,6-tetramethylpiperidinyl-1-oxyl radicals, and combinations thereof.

3. The dental composite composition of claim 1, wherein the polymerizable stable radical comprises:

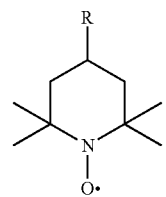

in which R is selected from the group consisting of: —Z, —XZ, —XY$_1$Z, —X(Z)(Z), —X(Y$_1$Z)(Y$_2$Z), —X(Z)(Z)(Z), and —X(Y$_1$Z)(Y$_2$Z)(Y$_3$Z);
wherein X, when present, is N, O, S, C—O, C—O—O, S—O, S—O—O, P—O, P—O—O, or P—O—O—O;
wherein Y$_1$, Y$_2$, and Y$_3$ are independently, when present, aryl or substituted aryl, linear or branched alkyl or aryl-alkyl; and
wherein Z, independently, is an unsaturated functional group.

4. The dental composite composition of claim 3, wherein Y$_1$, Y$_2$, and Y$_3$ are independently (CH$_2$)$_n$; (CH$_2$CH$_2$O)$_n$; or (CH$_2$CHCH$_3$O)$_n$, with n=0-20.

5. The dental composite composition of claim 3, wherein Z, independently, is vinyl, acrylamide, methacrylamide, acrylate, or methacrylate.

6. The dental composite composition of claim 3, wherein the polymerizable stable radical comprises a compound selected from the group consisting of:

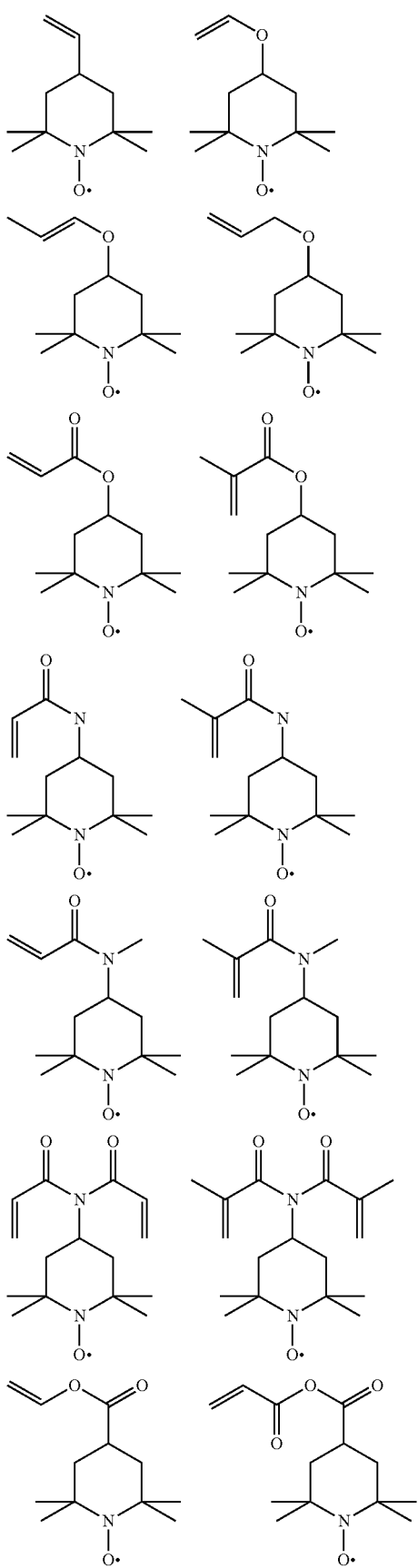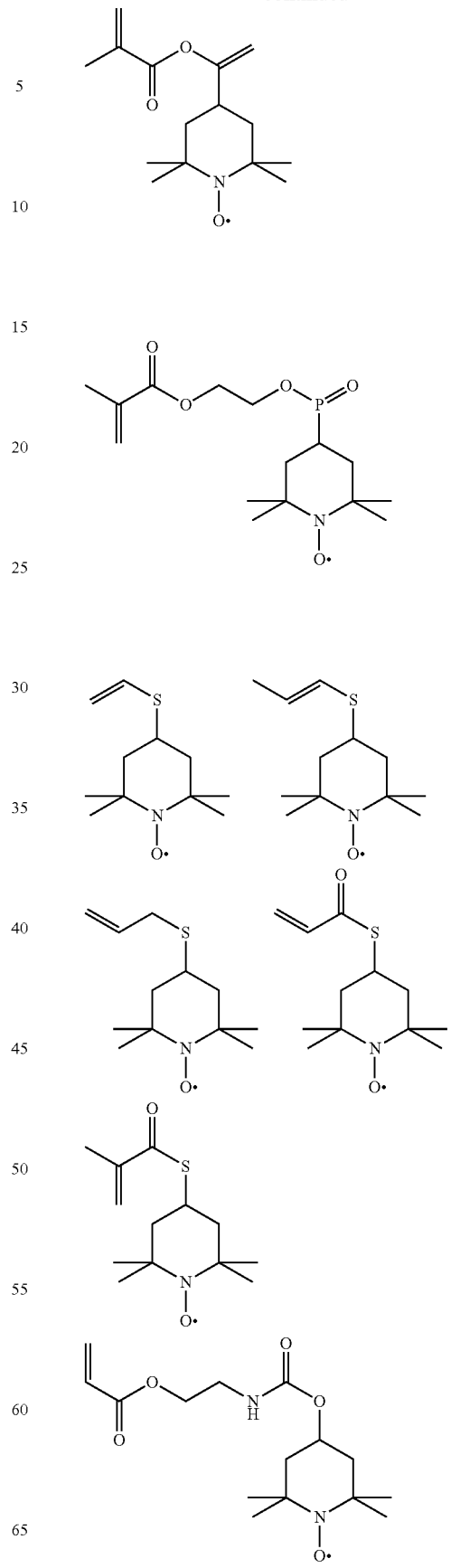

| 21 -continued | 22 -continued |
|---|---|
| 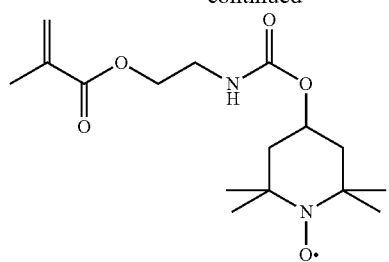 | 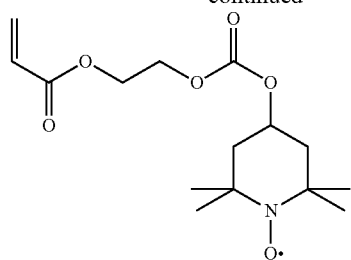 |
| 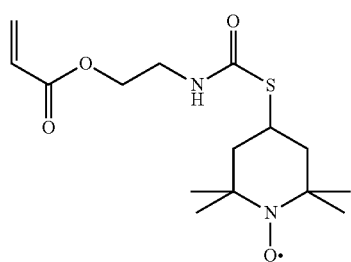 | 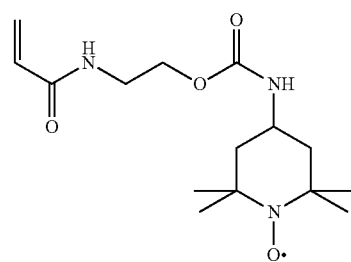 |
| 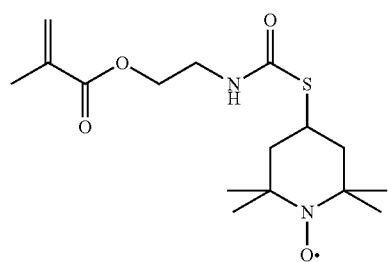 | 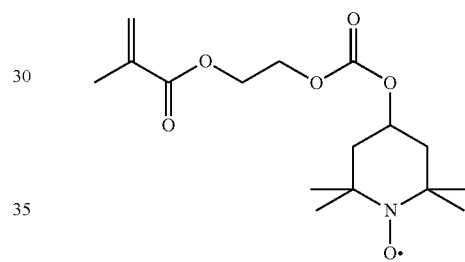 |
| 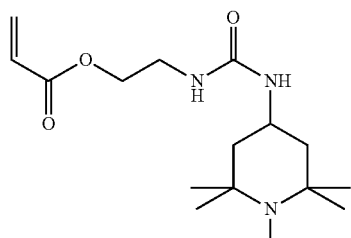 | 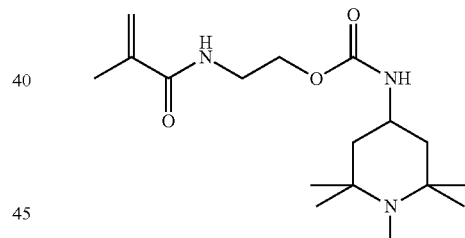 |
| 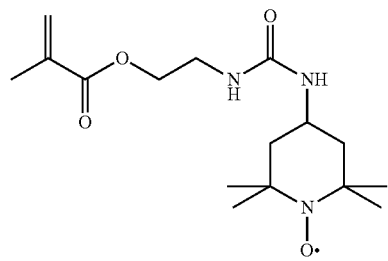 | 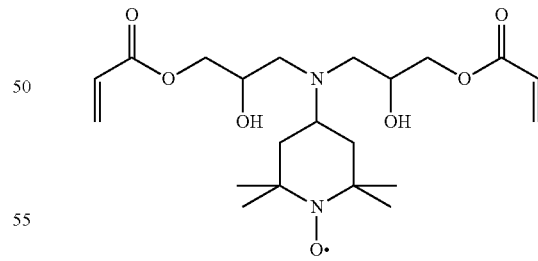 |
| 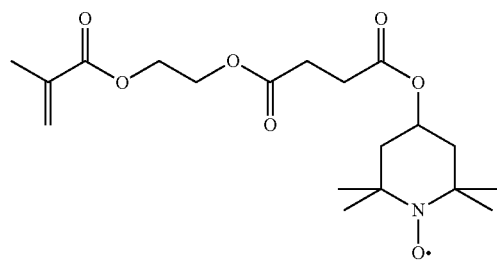 | 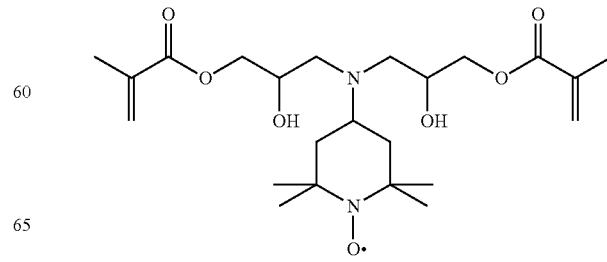 |

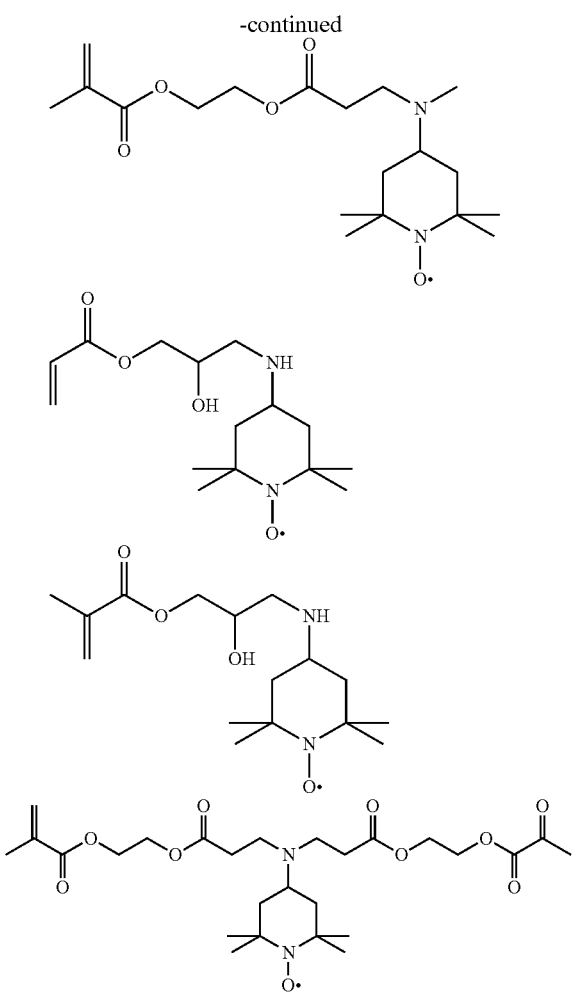

and combinations thereof.

7. The dental composite composition of claim 3, wherein the polymerizable stable radical comprises N,N-Bis-(3-oxa-4-oxo-6-methacryloyloxyhexyl)-4-amino-2,2,6,6 tetramethylpiperdin-1-oxyl radical.

8. The dental composite composition of claim 1, wherein the polymerizable stable radical is present from about 0.03 percent by weight to about 1 percent by weight of the dental composite composition and the polymerizable stable radical reduces shrinkage stress of the dental composite composition caused by polymerization by 20% or greater.

9. The dental composite composition of claim 1, wherein the free-radically polymerizable (meth)acrylate resin comprises a compound selected from the group consisting of 2,2-bis[4-(2-hydroxy-3-methacryloyloxypropoxy)phenyl] propane (Bis-GMA), 1,6-bis(2-methacryloxyethoxycarbonylamino)-2,4,4-trimethylhexane (UDMA), 2,2-bis[4-(methacryloyloxy-ethoxy)phenyl] propane (or ethoxylated bisphenol A-dimethacrylate) (EBPADMA), isopropyl methacrylate, triethyleneglycol dimethacrylate, diethyleneglycol dimethacrylate, tetraethyleneglycol dimethacrylate, 3-(acryloyloxy)-2-hydroxypropyl methacrylate, 1,3-propanediol dimethacrylate, 1,6-hexanediol di(meth)acrylate, 1,12-dodecanediol dimethacrylate, pentaerythritol triacrylate, pentaerythritol tetraacrylate, pentaerythritol tetramethacrylate, and combinations thereof.

10. The dental composite composition of claim 1, further comprising a photoinitiator.

11. The dental composite composition of claim 1, wherein the filler particles are present at about 90 percent or less by weight of the dental composite composition.

12. The dental composite composition of claim 11, wherein the filler particles comprise a mixture of micron-sized radiopaque filler particles and nano-sized filler particles.

13. A dental composite composition comprising:
a free-radically polymerizable resin selected from the group consisting of 2,2-bis[4-(2-hydroxy-3-methacryloyloxypropoxy)phenyl] propane (Bis-GMA), 1,6-bis(2-methacryloxyethoxycarbonylamino)-2,4,4-trimethylhexane (UDMA), 2,2-bis[4-(methacryloyloxy-ethoxy)phenyl] propane (or ethoxylated bisphenol A-dimethacrylate) (EBPADMA), isopropyl methacrylate, triethyleneglycol dimethacrylate, diethyleneglycol dimethacrylate, tetraethyleneglycol dimethacrylate, 3-(acryloyloxy)-2-hydroxypropyl methacrylate, 1,3-propanediol dimethacrylate, 1,6-hexanediol di(meth)acrylate, 1,12-dodecanediol dimethacrylate, pentaerythritol triacrylate, pentaerythritol tetraacrylate, pentaerythritol tetramethacrylate, and combinations thereof;

75 to about 90 percent by weight filler particles;

about 0.05 to about 1 percent by weight photoinitiator; and about 0.005 percent to about 5 percent by weight of a polymerizable stable radical containing a 2,2,6,6-tetramethylpiperidinyl-1-oxyl moiety and having the following formula:

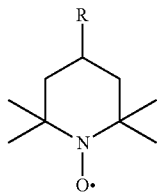

in which R is selected from the group consisting of: —Z, —XZ, —XY$_1$Z, —X(Z)(Z), —X(Y$_1$Z)(Y$_2$Z), —X(Z)(Z)(Z), and —X(Y$_1$Z)(Y$_2$Z)(Y$_3$Z);

wherein X, when present, is N, O, S, C—O, C—O—O, S—O, S—O—O, P—O, P—O—O, or P—O—O—O;

wherein Y$_1$, Y$_2$, and Y$_3$ are independently, when present, aryl or substituted aryl, linear or branched alkyl or aryl-alkyl;

wherein Z, independently, is an unsaturated functional group;

wherein the dental composite composition has a flexural modulus after polymerization of about 9500 MPa or greater; and wherein the polymerizable stable radical reduces shrinkage stress of the dental composite composition caused by polymerization by 10% or greater.

14. The dental composite composition of claim 13, wherein the polymerizable stable radical is selected from the group consisting of:

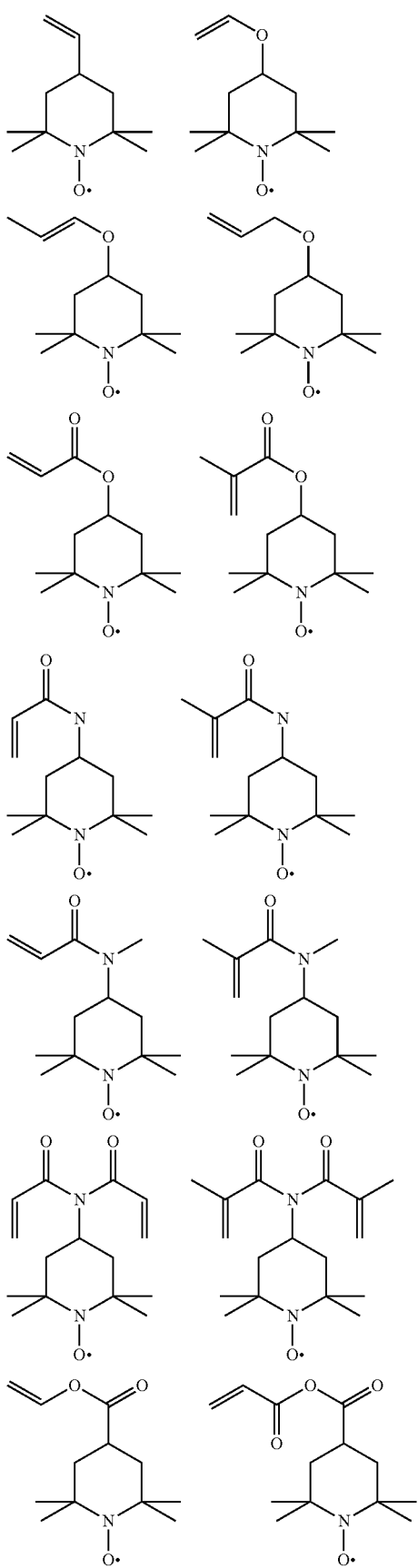
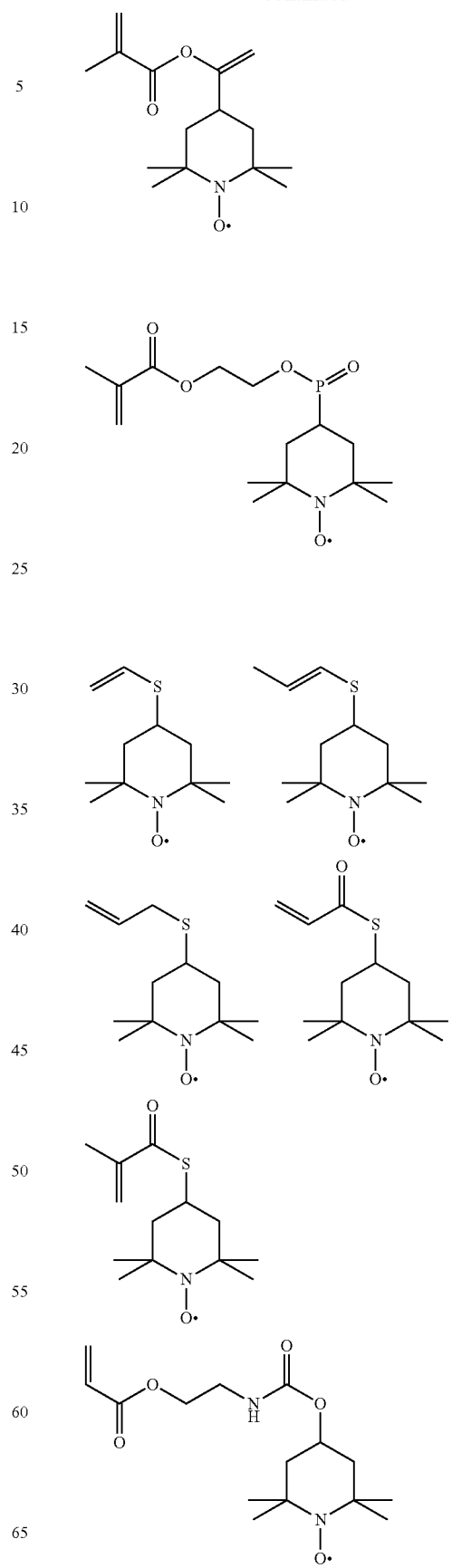

27
-continued
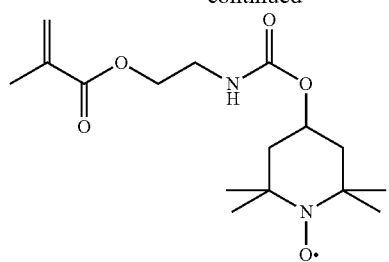
28
-continued
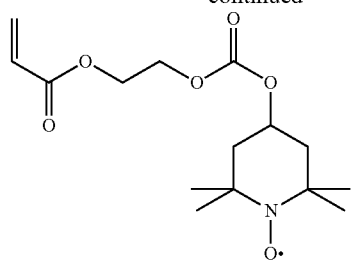
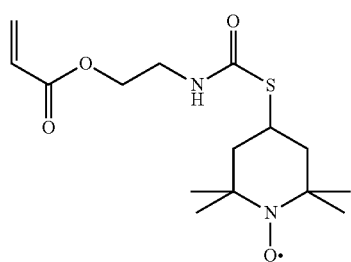
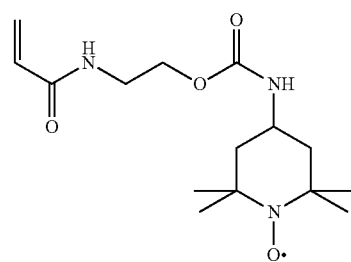
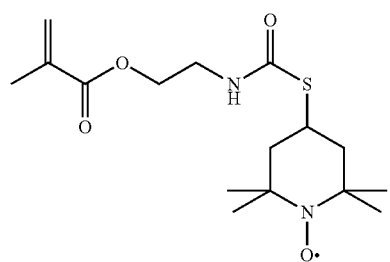
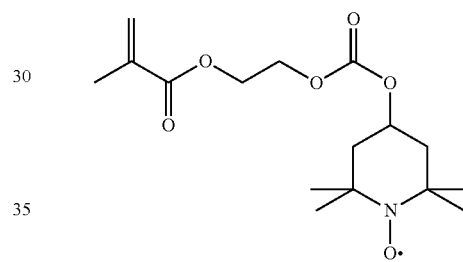
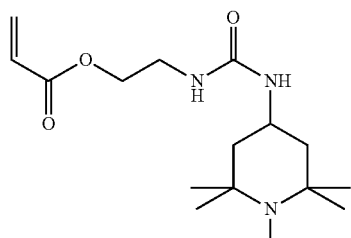
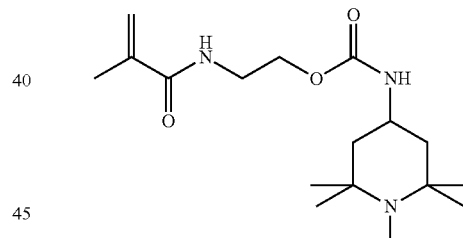
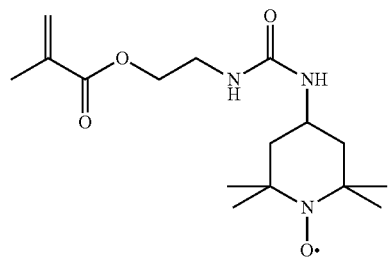
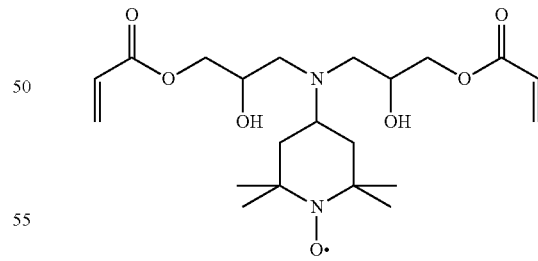
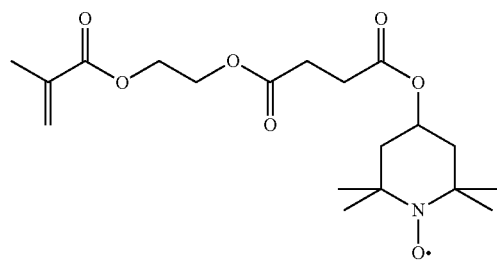
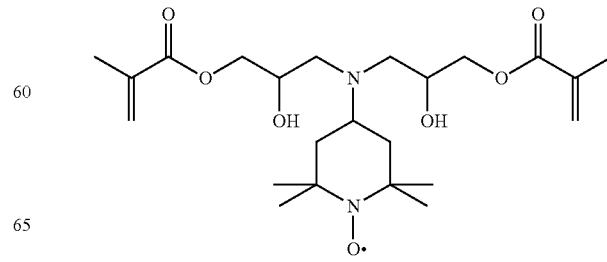

-continued

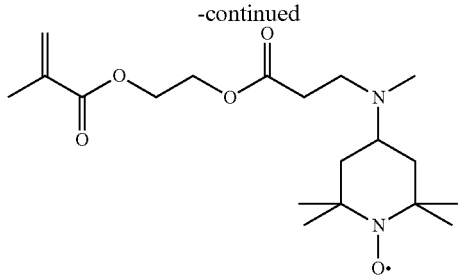

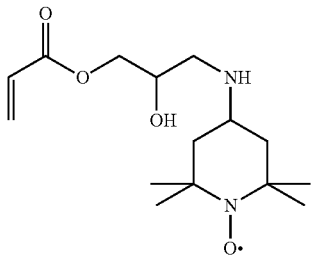

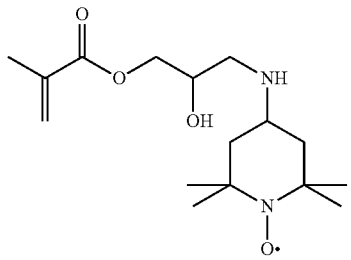

-continued

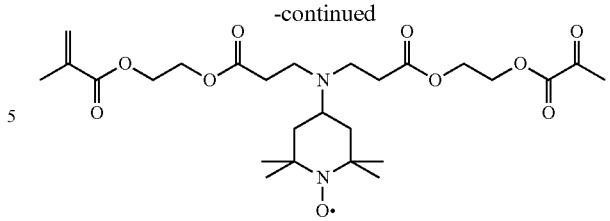

and combinations thereof.

15. The dental composite composition of claim 13, wherein the polymerizable stable radical is present from about 0.015 percent by weight to about 3 percent by weight of the dental composite composition.

16. The dental composite composition of claim 13, wherein the polymerizable stable radical comprises N,N-Bis-(3-oxa-4-oxo-6-methacryloyloxyhexyl)-4-amino-2,2,6,6 tetramethylpiperdin-1-oxyl radical.

17. The dental composite composition of claim 13, wherein the filler particles comprise a mixture of micron-sized radiopaque filler particles and nanofiller particles.

18. The dental composite composition of claim 1 comprising 80 percent by weight or greater of filler particles, the dental composite composition having a flexural modulus after polymerization of about 10300 MPa or greater.

19. The dental composite composition of claim 1, wherein the dental composite composition has a flexural strength after polymerization of about 140 MPa or greater.

20. The dental composite composition of claim 1, wherein the polymerizable stable radical is present from about 0.016 percent by weight to about 0.3 percent by weight of the dental composite composition.

* * * * *